United States Patent [19]

Means, Jr. et al.

[11] Patent Number: 5,311,023

[45] Date of Patent: May 10, 1994

[54] FILTER INSPECTION APPARATUS

[76] Inventors: Orville D. Means, Jr., 25570 Highway 79, San Ysabel, Calif. 92070; Milton L. Goff, 23945 Nectar Way, Ramona, Calif. 92065

[21] Appl. No.: 959,700

[22] Filed: Oct. 13, 1992

[51] Int. Cl.$^5$ ............................................. G01N 21/88
[52] U.S. Cl. ................................. 250/349; 250/341; 250/360.1
[58] Field of Search ................. 250/341, 358.1, 360.1, 250/349

[56] References Cited

U.S. PATENT DOCUMENTS

| | | | |
|---|---|---|---|
| 2,516,680 | 7/1950 | Culpepper | 183/61 |
| 3,800,157 | 3/1974 | Nichols | 250/341 |
| 3,840,402 | 10/1974 | Tobin, III | 134/29 |
| 4,048,500 | 9/1977 | Moore | 250/351 |
| 4,279,508 | 7/1981 | Everroad | 356/237 |
| 4,704,144 | 11/1987 | LeBlanc | 55/300 |
| 4,808,234 | 2/1989 | McKay | 134/21 |
| 4,842,624 | 6/1989 | Barton | 55/291 |
| 5,143,529 | 9/1992 | Means, Jr. | 55/290 |

FOREIGN PATENT DOCUMENTS

| | | | |
|---|---|---|---|
| 5830 | 3/1978 | Japan | 250/341 |
| 48236 | 2/1992 | Japan | 250/341 |
| 1474459 | 4/1989 | U.S.S.R. | 250/341 |

Primary Examiner—Carolyn E. Fields
Attorney, Agent, or Firm—Baker, Maxham, Jester & Meador

[57] ABSTRACT

A filter inspection apparatus for inspecting filters comprises a support frame for supporting a substantially tubular filter having inner and outer surfaces for rotation about its axis, a source of EMR for directing radiation along one of the inner and outer surfaces of a filter, an EMR sensing unit mounted adjacent to the other of the surfaces for sensing EMR passing through the filter and generating a signal, and an indicator responsive to the signal for indicating passage of EMR through the filter.

13 Claims, 3 Drawing Sheets

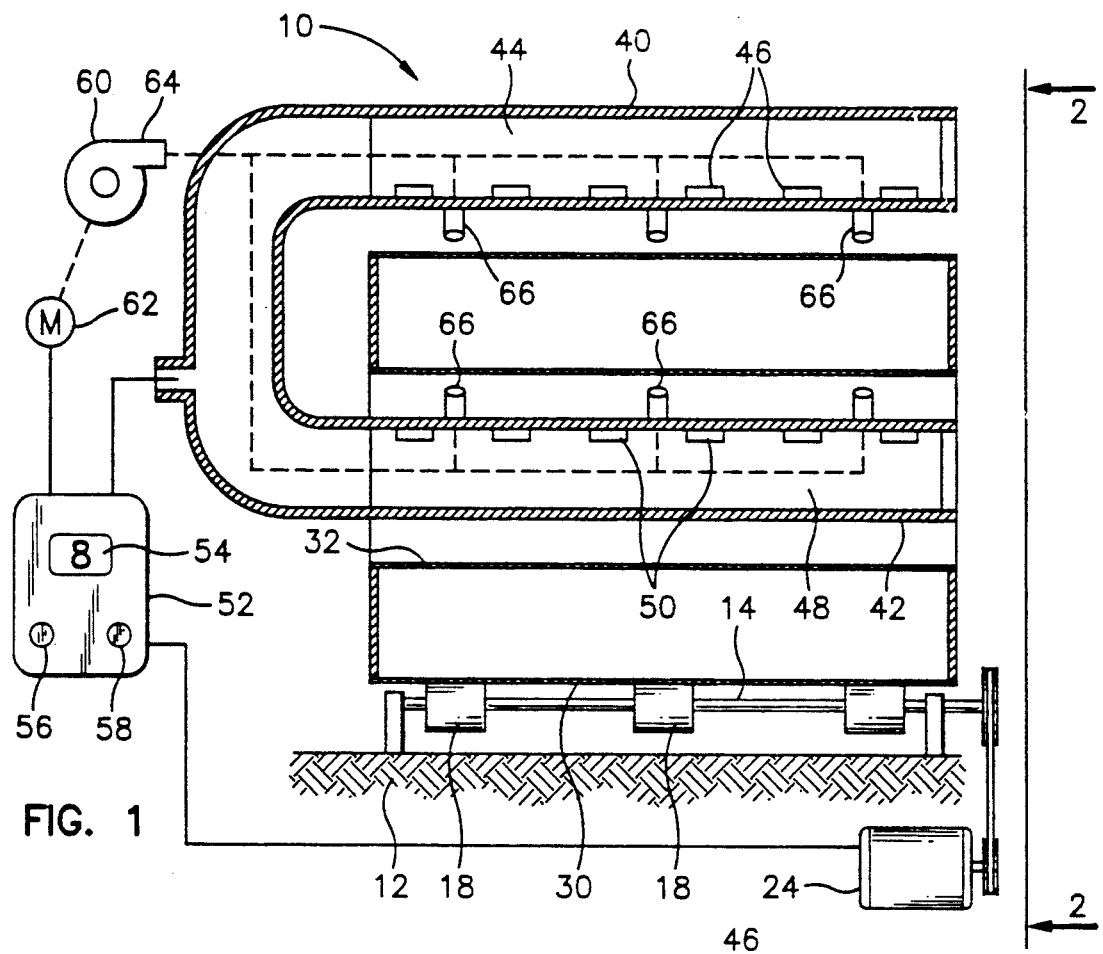
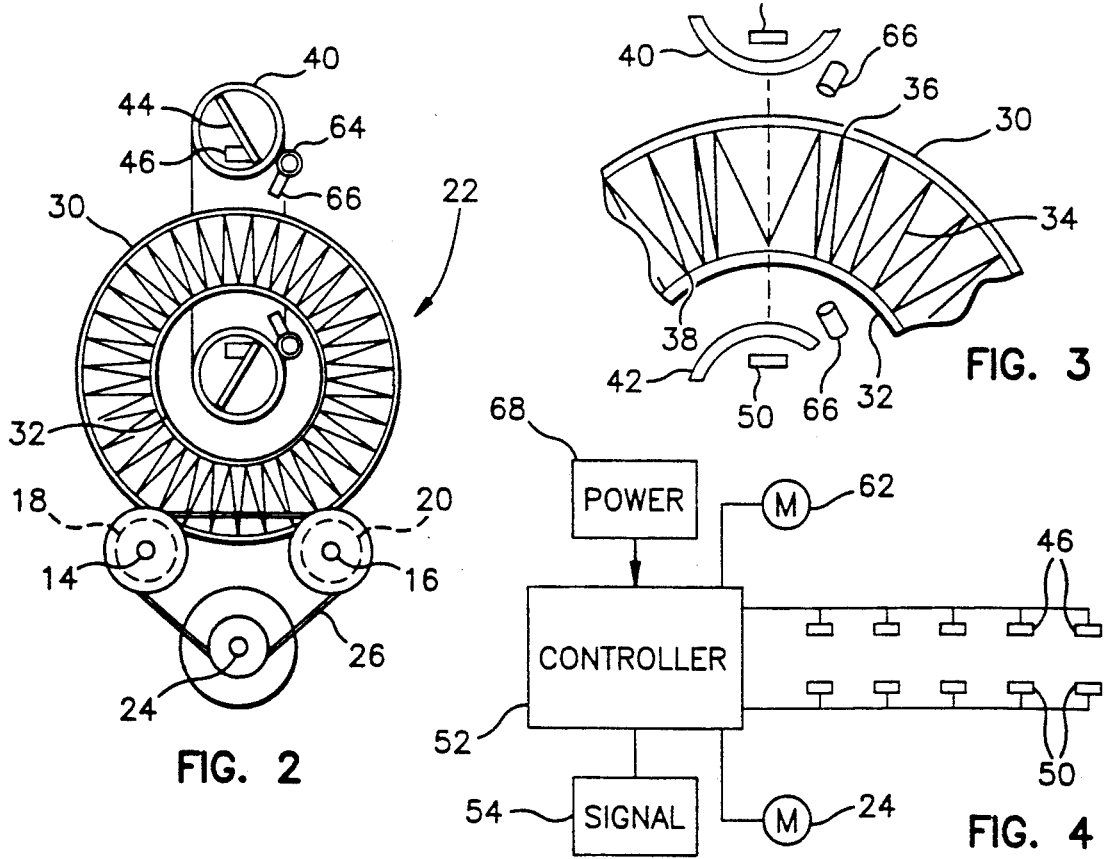
FIG. 1
FIG. 2
FIG. 3
FIG. 4

5,311,023

FILTER INSPECTION APPARATUS

BACKGROUND OF THE INVENTION

The present invention relates to inspection apparatus and pertains particularly to an improved filter inspection apparatus.

Internal combustion engines, gas turbines, and other air breathing machines are subject to damage from dirt, grit and the like that gets into the intake combustion air that they breathe. Therefore, they must have source of intake air that is clean and free of dirt, grit and debris. Most such machines utilize filters to filter dirt, grit and other debris from the air drawn into the machinery. Most such filters currently in use are of a large cylindrical tubular configuration, with some being tapered somewhat.

The filters are typically formed of inner and outer wire mesh or perforated metal screens, with a corrugated paper filter therebetween. The filter paper is formed to have a large surface area to allow the passage of air but to trap fine dirt and grit particles. The filter paper is typically formed with a fan or corrugated fold in order to provide a large surface area for the passage of large volumes of air and entrapment of dirt and grit particles. These filters typically cost between thirty-five and eighty-five dollars each. Therefore, filter replacement can become quite expensive when operating in dirty and dusty environments, such as mining and other earth working environments.

It has been customary in the past to clean the filters a limited number of times by washing them in a solvent or the like. The filters can be typically cleaned in this manner two to three times before they must be discarded.

A system has been recently developed as set forth in U.S. Pat. No. 5,143,529 granted to co-inventor Means herein that further extends the life of filters. That system provides a dry process for cleaning filters that enables them to be cleaned multiple times with no perceptible damage. However, filters do develop small holes from various sources, including cleaning and reuse that render them unusable. These small holes can let sufficient dirt or grit through to severely damage an engine. They usually develop in the crease or fold of the filter paper and are difficult to detect by traditional visual inspection.

Visual inspection of the filters is the most common form. However, such visual inspection is subject to the good eyesight, skill and concentration of the inspector. It is also subject to human error and judgment.

It is desirable that improved apparatus and methods be available to reliably inspect filters.

SUMMARY AND OBJECTS OF THE INVENTION

It is the primary object of the present invention to provide an improved filter inspection apparatus.

In accordance with a primary aspect of the present invention, a filter inspection apparatus for inspecting generally cylindrical filters comprises means for supporting a filter, a source of infrared (IR) radiation for directing against one surface of the filter, air nozzle means mounted for movement with said IR source along the surface of a filter for spreading the folds of the filter, and IR sensing means on the opposite side of the filter for detecting the passage of IR therethrough.

BRIEF DESCRIPTION OF THE DRAWING

The above and other objects and advantages of the present invention will become apparent from the following description when read in conjunction with the accompanying drawings wherein:

FIG. 1 is a side diagrammatic elevation view of a preferred embodiment of the invention;

FIG. 2 is a right side end view of the embodiment of FIG. 1;

FIG. 3 is an enlarged partial sectional view of a portion of FIG. 2;

FIG. 4 is a functional block diagram of the control system of the invention;

DETAILED DESCRIPTION OF A PREFERRED EMBODIMENT

Figure 5:
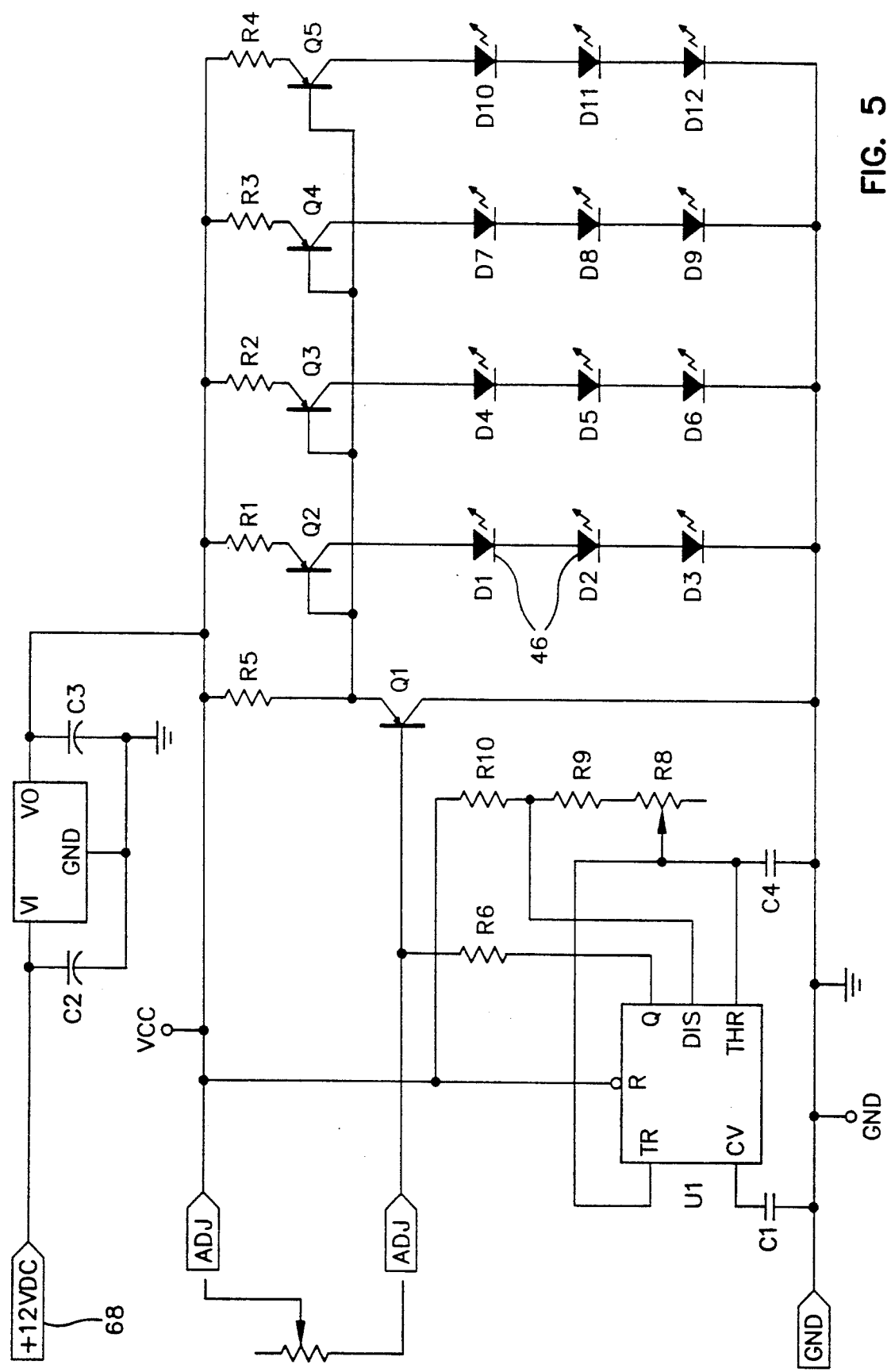
FIG. 5 is a schematic diagram of the IR transmitter.

Referring to FIGS. 1 and 2 of the drawings, diagrammatic illustration of an exemplary embodiment of the invention is shown and designated generally by the numeral 10. The illustrated embodiment comprises a generally horizontally extending support frame structure of a somewhat generally rectangular construction.

The illustrated apparatus, designated generally by the numeral 10, comprises a suitable base frame 12 having suitable support or mounting means for a filter, such as a pair of spaced apart shafts 14 and 16, on which are mounted a plurality of rollers 18 and 20. At least some of these rollers are preferably keyed or fixed to the shaft to rotate therewith and cause rotation of a filter, designated generally at 22, when said filter is supported thereon. A suitable motor, such as an electrical motor 24, drives the shafts through a belt 26 and pulley 28.

The apparatus, as illustrated, is designed primarily to inspect larger tubular type air filters which are typically used in large trucks and earth moving equipment. Such filters are preferably cleaned for reuse and recycling in machines, such as disclosed in the aforementioned Means' patent which is incorporated herein by reference as though fully set forth. These filters are typically constructed of outer and inner wire mesh cylinders 30 and 32 between which is disposed a filter paper folded in an accordion or fan fold fashion, as illustrated in FIGS. 2 and 3. This folding provides a large surface area of panels between folds for trapping dust, grit and debris. The filter paper insert is folded to form and define outer folds 36 and inner folds 38 where holes typically occur. The present invention is designed to inspect filters and locate these holes with minimum error. Many times the holes can be patched by suitable doping compound, thereby enabling reuse and considerable savings in costs and expenses to a vehicle operator.

The apparatus comprises means for detecting holes in the filter by means of electro magnetic radiation (EMR), preferably in the form of infrared (IR) radiation directed against one surface of the filter, and means for detecting passage of the IR through the filter on the other side of the filter surface. An exemplary embodiment of the apparatus comprises support structure, which in the illustrated embodiment comprises a generally U-shaped transparent tube formed of a transparent plastic or glass or the like. It may also be of other materials with transparent windows, if desired.

In the illustrated embodiment, the support member has an outer arm 40 for extending along an outer surface of a filter, and an inner arm 42 for extending into the bore of a filter. An electronic IR transmission circuit is formed principally on a PC board 44, and disposed or mounted within the outer tube arm 40. This IR transmission circuit includes a plurality of IR diodes 46 mounted within the upper tube 40, and positioned to direct IR radiation against the outer surface of the filter. In the preferred form, the IR emitter diodes 44 are distributed continuously along the length of the tube, which is preferably long enough to accommodate the largest filter to be inspected. An exemplary embodiment contains two-hundred sixteen IR emitters for accommodating a twenty-four inch long filter. It is also possible to utilize a single emitter or small group of emitters mounted on a moveable arm to move along the axis of the filter.

An IR receiver circuit is formed on a PC board 48 mounted within the tube 42, and containing a plurality of IR receivers or sensors 50 disposed therealong, preferably grouped into two inch intervals, each containing seven. The transmitter and receiver circuits are preferably wired to a controller 52. The controller 52 may be simple switching controls, but preferably includes a CPU and suitable means for providing a signal, such as a digital readout at 54 of the sensor which senses the transmission of IR. It may also preferably include means to stop the drive instantaneously as IR is sensed, so that a hole or opening in the filter may be readily located. The receivers or group of receivers are preferably numerically identified in sequence, such as for example starting at the outer end with one and numerically numbered up to the final number toward the left hand end of the apparatus as shown in FIG. 1. Thus, a sensor eight or group of sensors eight sensing the transmission of IR will cause the controller to display the digit eight on the readout 54. The operator can then locate the hole at or near the number eight sensor or group of sensors. The controller 52 may include two or more switches 56 and 58 for power and for activation of the system generally. In the alternative, the system may be entirely manually controlled with switches for turning on and off the various circuits, and light indicators indicating the respective source of sensing IR.

The apparatus is preferably provided with a source of pressurized air, which for example may be a blower or compressor 60 driven by a motor 62 for blowing air by way of a suitable conduit 64, and a plurality of ports or nozzles 66 onto the outer, inner or both surfaces of the filter. The apparatus is shown with a source of air blowing on both surfaces of the filter which causes the filter folds to separate, as shown in FIG. 3, to more clearly expose openings at either the outer or inner folds of the paper filter element. The air will separate the fold panels as shown in FIG. 3 as the filter rotates, thus providing a greater expose of the edges of the filter unit to the IR. This provides a more reliable chance that a tear or hole in the filter will be detected by the passage of IR radiation therethrough. The system may be powered by a suitable external power source or by batteries 68, as designated in FIG. 4. The air source may also be a blower or compressor incorporated in the apparatus or may be from an external source. For example, most automotive repair shops have large compressors with ample source of compressed air.

Figure 6:
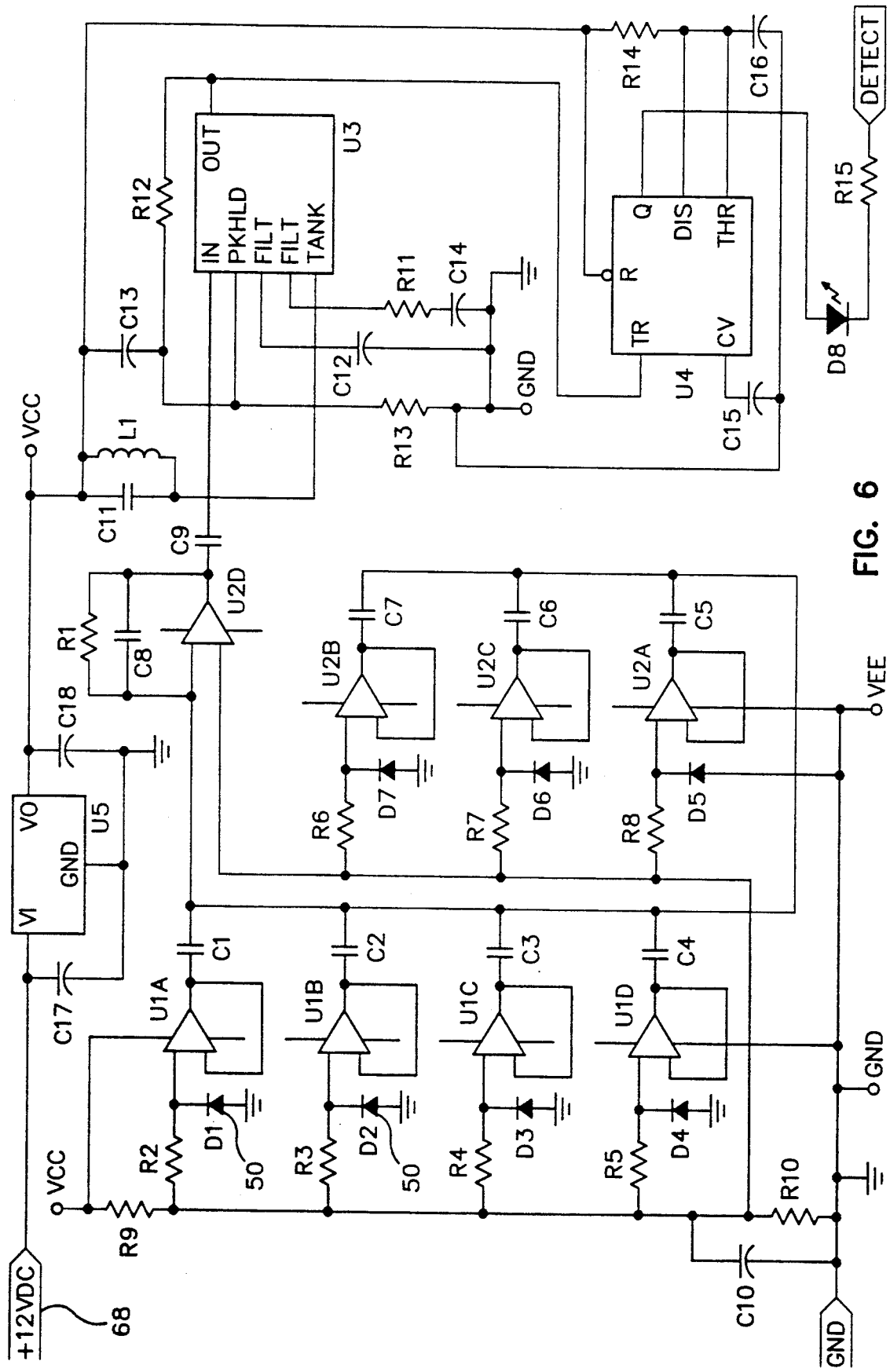
FIG. 6 is a schematic diagram of the IR detector circuit.

Referring to FIGS. 5 and 6, there is illustrated respectively schematic diagrams of the transmitter circuit and the receiver circuit. These are circuits for an actual prototype constructed and tested.

Referring to FIG. 5, a schematic of an exemplary embodiment of the IR transmitter circuit is illustrated. The construction and function of this circuit will be apparent to one of ordinary skill in the art from the illustrated schematic using standard symbols for circuit elements. The circuit is powered by a twelve volt DC source 68 and has means including provisions for adjustment for powering or activating a plurality of light emitting diodes D1-D12 (LEDs defining emitters 46). The circuit includes means causing the LEDs to modulate at fifty kilohertz (kHz) to overcome background IR. Other frequencies of modulation may be selected if desired.

Referring to FIG. 6, a schematic of an IR detector circuit is illustrated. The construction and operation of the IR receiver circuit will be apparent from the illustrated schematic to one of ordinary skill in the art. The circuit is powered by a twelve volt DC source (e.g. 68), and has a plurality of IR receivers or sensors 50 that sense the IR modulated at fifty kilohertz, and amplifies and transmits a signal to the detector or signal circuit. The detectors when sensing IR generate an electrical signal which is amplified and transmitted via the circuit to the detector. Thus, when an IR signal modulated at fifty kilohertz is detected, a signal indicative of a hole in a filter is indicated. The rotation of the filter is immediately stopped, and the hole in the filter visually located and either repaired or the filter discarded.

Thus, in operation as filters are cleaned by a suitable process, such as in the aforementioned patent, the cleaned filter is inspected by mounting in an apparatus as above described. The filter is supported on rollers 18 and 20, and the apparatus activated so as to rotate the filter as the IR transmission circuit is activated. If IR radiation passes through the filter and is detected by the detection circuit, a signal is indicated to the operator who then immediately stops the rotation of the filter and locates the hole visually. He may then, as previously stated, either repair the hole in the filter or discard the filter.

While the present invention was developed for inspecting generally tubular, including somewhat conical filters, it is apparent that with minor modifications I can also inspect non-tubular filters. For example, certain filters exist which have a generally V-trough configuration. These, and others having either a curved (i.e. semi-circular) or flat planar configuration can be inspected by slight modifications to the filter support and limiting the rotation of the filter clamp or support to an oscillation. The filters can be mounted in the machine and moved so that the sensing and transmitting heads move along the opposed faces thereof while cleaning. It will also be apparent that the inspection apparatus can be incorporated into a cleaning device as disclosed the aforementioned patent.

While we have illustrated and described our invention by means of specific embodiments, it should be understood that numerous changes and modifications may be made therein without departing from the spirit and scope of the invention as defined in the appended claims.

We claim:

1. A filter inspecting apparatus for inspecting generally tubular filters, comprising:
   a support frame;

mounting means mounted on said support frame for supporting a substantially tubular filter having inner and outer surfaces for rotation about its axis;

a source of IR mounted for directing radiation along one of said inner and outer surface of the filter;

IR sensing means mounted adjacent to the other of said inner and outer surfaces for sensing IR passing through said filter and generating a signal responsive thereto;

indicator means responsive to said signal for indicating passage of IR through said filter; and means for directing air against one of said surfaces during inspecting of said filter for separating folds therein.

2. A filter inspecting apparatus according to claim 1 further comprising means for rotating said filter during inspecting for directing said radiation along said one of said inner and outer surface of the filter.

3. A filter inspecting apparatus according to claim 2 wherein said IR is pulsed at about 50 kHz for distinguishing over ambient sources of IR.

4. A filter inspecting apparatus according to claim 1 wherein said source of IR comprises a plurality of IR transmitters mounted along an elongated support member for extending along parallel the axis of the filter for directing said radiation along said one of said inner and outer surface of the filter.

5. A filter inspecting apparatus according to claim 1 wherein said IR sensing means comprises a plurality of IR sensing elements mounted along the length of an elongated support member.

6. A filter inspecting apparatus according to claim 5 wherein said IR sensing means comprises a plurality of IR sensing elements grouped at intervals along the length of said support member.

7. A filter inspecting apparatus for inspecting generally tubular filters, comprising:

a support frame;

mounting means mounted on said support frame for supporting a substantially tubular filter having inner and outer surfaces for rotation about its axis;

a source of IR mounted for directing radiation along one of said inner and outer surface of a filter, said IR source is pulsed at about 50 kHz for distinguishing over ambient sources of IR;

IR sensing means mounted adjacent to the other of said inner and outer surfaces for sensing IR passing through said filter and generating a signal responsive thereto;

indicator means responsive to said signal for indicating passage of IR through said filter; and further comprising means for directing air against one of said surfaces of said filter during inspecting for separating folds therein.

8. A filter inspecting apparatus according to claim 7 further comprising means for rotating said filter.

9. A filter inspecting apparatus according to claim 7 wherein said source of IR comprises a plurality of IR transmitters mounted along an elongated support member for extending along substantially parallel to the axis of the filter for directing radiation along one of said inner and outer surface of a filter.

10. A filter inspecting apparatus according to claim 9 wherein said IR sensing means comprises a plurality of IR sensing elements mounted along the length of a support member for extending along substantially parallel to the axis of the filter for sensing IR.

11. A filter inspecting apparatus according to claim 7 wherein said IR sensing means comprises a plurality of IR sensing elements mounted along the length of an elongated support member.

12. A filter inspecting apparatus according to claim 11 wherein said IR sensing means comprises a plurality of IR sensing elements grouped at intervals along the length of said support member.

13. A filter inspecting apparatus comprising:

a support frame;

mounting means on said support frame for supporting a substantially tubular filter having an inner surface and an outer surface for rotation about its axis, said mounting means including roller means for engaging the outer surface of the filter for supporting same for rotation about a horizontal axis;

means for rotating said roller means for rotating said filter during inspection thereof;

means for directing air against one of said surfaces of said filter during inspection for separating folds therein;

a source of IR radiation comprising a plurality of IR transmitters mounted at spaced intervals along an elongated support member for directing radiation along one of said inner and outer surface of a filter;

IR radiation sensing means comprising a plurality of IR sensors mounted at spaced intervals along an elongated support member adjacent to the other of said inner and outer surfaces for sensing IR radiation passing through said filter and generating a signal responsive thereto; and indicator means responsive to said signal for indicating passage of IR radiation through said filter.

* * * * *